US010201715B2

(12) United States Patent
Wang et al.

(10) Patent No.: US 10,201,715 B2
(45) Date of Patent: Feb. 12, 2019

(54) MAGNETIC NANOSTIMULATOR AND NANOSENSOR ARRAY FOR BIOLOGICAL MATERIAL STIMULATION AND SENSING

(71) Applicant: Regents of the University of Minnesota, Minneapolis, MN (US)

(72) Inventors: Jian-Ping Wang, Shoreview, MN (US); Walter C. Low, Minneapolis, MN (US); Mahendra DC, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 321 days.

(21) Appl. No.: 15/130,371

(22) Filed: Apr. 15, 2016

(65) Prior Publication Data

US 2016/0303392 A1      Oct. 20, 2016

Related U.S. Application Data

(60) Provisional application No. 62/148,053, filed on Apr. 15, 2015, provisional application No. 62/148,465, filed on Apr. 16, 2015.

(51) Int. Cl.
*A61N 2/00* (2006.01)
*B82Y 5/00* (2011.01)
*B82Y 15/00* (2011.01)

(52) U.S. Cl.
CPC ............... *A61N 2/006* (2013.01); *B82Y 5/00* (2013.01); *B82Y 15/00* (2013.01)

(58) Field of Classification Search
CPC ........... A61N 2/006; B82Y 5/00; B82Y 15/00
See application file for complete search history.

(56) References Cited

U.S. PATENT DOCUMENTS

| | | | |
|---|---|---|---|
| 6,678,562 B1 * | 1/2004 | Tepper | A61B 17/6416 606/54 |
| 8,954,166 B2 | 2/2015 | Pettinelli | |
| 2010/0324642 A1 * | 12/2010 | Pettinelli | A61N 1/0556 607/118 |
| 2015/0209586 A1 | 7/2015 | Silva et al. | |

FOREIGN PATENT DOCUMENTS

| | | |
|---|---|---|
| CN | 204121602 U | 1/2015 |
| WO | 2015153868 A1 | 10/2015 |

OTHER PUBLICATIONS

Pong et al., Hysteresis loop collapse for linear response in magnetic-tunnel-junction sensors, Journal of Applied Physics, vol. 105, pp. 07E723-1-07E723-3, 2009.
Pundt et al., Transplantation of human striatal tissue into a rodent model of Huntington's Disease: phenotypic expression of transplanted neurons and host-to-graft innervation, Brain Research Bulletin, vol. 39, No. 1, pp. 23-32, 1996.
(Continued)

*Primary Examiner* — Charles A Marmor, II
*Assistant Examiner* — Joshua D Lannu
(74) *Attorney, Agent, or Firm* — Westman, Champlin & Koehler, P.A.; Theodore M. Magee (57) ABSTRACT

An apparatus includes a substrate and a plurality of biological material stimulators positioned on the substrate. Each biological material stimulator forms a fluctuating magnetic field capable of inducing a current in biological material.

20 Claims, 11 Drawing Sheets

(56) References Cited

OTHER PUBLICATIONS

Rahman et al., Reduction of switching current density in perpendicular magnetic tunnel junctions by tuning the anisotropy of the CoFeB free layer, Journal of Applied Physics, vol. 11, pp. 07C907-1-07C907-3, 2012.
Reinhoud et al., Analysis of glutamate, GABA, noradrenaline, dopamine, serotonin, and metabolites using microbore UHPLC with electrochemical detection, ACS Chemical Neuroscience, vol. 4, pp. 888-894, 2013.
Riklin et al., Glucose and acetylcholine sensing multilayer enzyme electrodes of controlled enzyme layer thickness, Anal. Chem., vol. 67, pp. 4118-4126, 1995.
Romani, Fundamentals on Neuromagnetism, Advances in Biomagnetism, pp. 33-46, 1989.
Rousche et al., Flexible polyimide-based intracortical electrode arrays with bioactive capability, IEEE Transactions on Biomedical Engineering, vol. 48, No. 3, pp. 361-371, 2001.
Roy et al., Biomedical applications of diamond-like carbon coatings: a review, Wiley, Interscience, pp. 72-84, 2006.
Rubehn et al., A MEMS-based flexible multichannel ECoG-electrode array, Journal of Neural Engineering, vol. 6, 10 pages, 2009.
Saltzberg et al., Pharmacological characterization of P2Y receptor subtypes on isolated tiger salamander muller cells, GLIA, vol. 42, pp. 149-159, 2003.
Shinwari et al., Microfabricated reference electrodes and their biosensing applications, Sensors, vol. 10, pp. 1679-1715, 2010.
Srinivasan et al., A detection system based on giant magnetoresistive sensors and high-moment magnetic nanoparticles demonstrates zeptomole sensitivity: potential for personalized medicine, Communications, Biosensors, Angew, Chem. Int. Ed., vol. 48, pp. 2764-2767, 2009.
Suh et al., Neurovascular coupling and oximetry during epileptic events, Molecular Neurobiology, vol. 33, pp. 181-197, 2006.
Tanghe et al., A 16-channel CMOS neural stimulating array, IEEE Journal of Solid-State Circuits, vol. 27, No. 12, pp. 1819-1825, 1992.
Tetienne et al., Nitrogen-vacancy-center imaging of bubble domains in a 6-A film of cobalt with perpendicular magnetization, Journal of Applied Physics, vol. 115, pp. 17D501-1-17D501-3, 2014.
Triarhou et al., Transplantation of ventral mesencephalic analgen to a genetic model of nigrostriatal dopamine deficiency, Proceedings of the National Acadamy of Science, vol. 83, pp. 8789-8793, 1986.
Van der Wel, MOSFET 1/f noise measurement under switched bias conditions, IEEE Electron Device Letters, vol. 21, No. 1, pp. 43-46, 2000.
Viventi et al., Flexible, foldable, actively multiplexed, high-density electrode array for mapping brain activity in vivo, Nature Neuroscience, Technical Reports, vol. 14, No. 12, pp. 1599-1607, 2011.
Weiland et al., In Vitro electrical properties for iridium oxide versus titanium nitride stimulating electrodes, IEEE Transactions on Biomedical Engineering, vol. 49, No. 12, pp. 1574-1579, 2002.
West et al., A simple model for calculating magnetic nano-wire domain wall fringing fields, Journal of Physics D: Applied Physics, vol. 45, pp. 1-9, 2012.
Wikipedia, https://en.wikipedia.org/wiki/neurostimulation, 2016.
Winkin et al., Flexible multi-electrode array with integrated bendable CMOS-chip for implantable systems, 34th Annual International Conference of the IEEE EMBS, pp. 3882-3885, 2012.
Wise et al., Microfabrication techniques for integrated sensors and microsystems, Science, pp. 1335-1342, 1991.
Wise et al., An integrated-circuit approach to extracellular microelectrodes, IEEE Transactions on Bio-Medical Engineering, vol. BME-17, No. 2, pp. 238-247, 1970.
Wise et al., Wireless implantable microsystems: high-density electronic interfaces to the nervous system, Proceesings of the IEEE, vol. 92, No. 1, pp. 76-97, 2004.
Woosley et al., The magnetic field of a single axon: a volume conductor model, Mathematical Biosciences, vol. 76, pp. 1-36, 1985.
Yao et al., Improved current switching symmetry of magnetic tunneling junction and giant magnetoresistance devices with nano-current-channel structure, Journal of Applied Physics, vol. 115, pp. 07A717-1-07A717-3, 2008.
Yue et al., Magneto-electric nano-particles for non-invasive brain stimulation, Open Access, PLOS One, vol. 7, No. 9, pp. 1-5, 2012.
Zhang et al., High power and low critical current spin torque oscillation from a magnetic tunnel junction with a built-in hard axis polarizer, Applied Physics Letters, vol. 100, pp. 032405-1-032405-4, 2012.
Hamalainen et al., Magnetoencephalography—therory, instrumentation, and applications to noninvasive studies of the working human brain, Reviews of the Modem Physics, vol. 65, No. 2, pp. 413-497, 1993.
Amaral et al., Towards a system to measure action potential on mice brain slice with local magneto resistive probes, Journal of Applied Physics 109, 07B308, 2011, 14 pages.
Banks, Neurotechnology, Engineering Science and Education Journal, 1998, pp. 135-144.
Barach et al., Magnetic Measurements of Action Currents in a Single Nerve Axon: A Core-Conductor Model, IEEE Transactions on Biomedical Engineering, vol. BME-32, No. 2, 1985, pp. 136-140.
Bartorelli et al., Aspirin Alone Antiplatelet Regimen After Intracoronary Placement of the Carbostent, Catheterization and Cardiovascular Interventions, vol. 55, pp. 150-156, 2002.
Berger, Motion of a Magnetic Domain Wall Traversed by Fast-Rising Current Pulses, Journal of Applied Physics, vol. 71, No. 6, pp. 2721-2726, 1992.
Bhowmik et al., Deterministic Domain Wall Motion Orthogonal to Current Flow Due to Spin Orbit Torque, Scientific Reports, 2015, 10 pages.
Bloom et al., 1/f noise reduction of metal-oxide-semiconductor transistors by cycling from inversion to accumulation, Applied Physics Letters, vol. 58, No. 15, pp. 1664-1666, 1991.
Bohning, Mapping transcranial magnetic stimulation (TMS) fields in vivo with MRI, Neuro Report, vol. 8, pp. 2535-2538, 1997.
Burmeister et al., Glutaraldehyde cross-linked glutamate oxidase coated microelectrode arrays: selectivity and resting levels of glutamate in the CNS, ACS Chemical Neuroscience, vol. 4, pp. 721-728, 2013.
Cardoso et al., Magnetic tunnel junction sensors with pTesla sensitivity, Microsystem Technology, 11 pages, 2013.
Chaves et al., MgO based picotesla field sensors, Journal of Applied Physics, vol. 103, pp. 07E931-1-07E931-3, 2008.
Chen et al., Direct electrochemical oxidation of NADPH at a low potential on the carbon nanotube modified glassy carbon electrode, Chinese Journal of Chemistry, vol. 22, No. 2, pp. 167-171, 2004.
Chen et al., Wireless magnetothermal deep brain stimulation, Research, Neurotechniques, vol. 347, No. 6229, pp. 1477-1480, 2015.
Cheung, Implantable microscale neural interfaes, Biomed Microdevices, vol. 9, pp. 923-938, 2007.
Clark et al., A Mathematical Evaluation of the Core Conductor Model, Biophysical Journal, vol. 6, pp. 95-112, 1966.
Cogan, Neural stimulation and recording electrodes, Annual Review of Biomedical Engineering, vol. 10, pp. 275-309, 2008.
Cogan et al., Sputtered Iridium Oxide Films (SIROFs) for Low-Impedance Neural Stimulation and Recording Electrodes, Proceedings of the 26th Annual International Conference of the IEEE EMBS, pp. 4153-4156, 2004.
Cohen, Magnetoencephalography: Evidence of Magnetic Fields Produced by Alpha-Rhythm Currents, Science, vol. 161, pp. 784-786, 1968.
Dey et al., Nanomaterial-based functional scaffolds for amperometric sensing of bioanalytes, Anal Bioanal Chemical, vol. 405, pp. 3431-3448, 2013.
Dichter, Rat cortical neurons in cell culture: culture methods, cell morphology, electrophysiology, and synapse formation, Brain Research, vol. 149, pp. 279-293, 1978.

(56) References Cited

OTHER PUBLICATIONS

Dierickx et al., The decrease of "random telegraph signal" noise in metal-oxide semiconductor field-effect transistors when cycled from inversion to accumulation, Journal of Applied Physics, vol. 71, No. 4, pp. 2028-2029, 1993.
Duan et al., Tauroursodeoxycholic acide improves the survival and function of nigral transplants in a rat model of Parkinson's disease, Cell Transplantation, vol. 11, pp. 195-205, 2002.
Enz et al., Circuit techniques for reduce the effects of op-amp imperfections: autozero, correlated double sampling, and chopper stabilization, Proceedings of the IEEE, vol. 84, No. 11, pp. 1584-1614, 1996.
Fukami et al., Current-induced domain wall motion in perpendicularly magnetized coFeB nanowire, Applied Physics Letters, vol. 98, pp. 082504-1-082504-3, 2011.
Grill-Spector et al., Differential processing of objects under various viewing conditions in the human lateral occipital complex, Neuron, vol. 24, pp. 187-203, 1999.
HajjHassan et al., NeuroMEMS: Neural Probe Microtechnologies, Sensors, vol. 8, pp. 6704-6726, 2008.
Hascup, Microelectrode array fabrication and optimzation for selective neurochemical detection, Microelectrode Biosensors, Neuromethods, vol. 80, pp. 27-54, 2013.
Intechopen, http://www.intechopen.com, accessed 2016.
Jang et al., Two distinct filopodia populations at the growth cone allow to sense nanotopographical extracellular matrix cues to guide neurite outgrowth, Open Access, Sensing of ECM Nanotopographical Cues by Filopodia, vol. 5, No. 12, 11 pages, 2010.
Jansen et al., Transplantation of fetal neocortex ameliorates sensorimotor and locomotor deficits following neonatal schemic-hypoxic brain injury in rats, Experimental Neurology, vol. 147, pp. 487-497, 1997.
Kassim et al., Tail current flicker noise reduction in LC VCOs by complementary switched biasing, ICM, pp. 102-105, 2003.
Kegley, Testing the efficiency of vertically aligned gold nanowires on a titanium needle implantable neural electrodes in the Rattus Norvegicus Hippocampus, University of Arkansas, ScholarWorks@UARK, Electrical Engineering Undergraduate Honors Theses, 41 pages, 2012.
Kim et al., Electroanalytical eavesdropping on single cell communication, Analytical Chemistry, vol. 83, pp. 7242-7249, 2011.
Kim et al., A low-noise WLAN mixer using switched biasing technique, IEEE Microwave and Wireless Components Letters, vol. 19, No. 10, pp. 650-652, 2009.
Lee et al., Polyimide-based intracortical neural implant with improved structural stiffness, Journal of Micromechanics and Microengineering, vol. 14, pp. 32-37, 2004.
Lee et al., Wheatstone bridge giant-magnetoresistance based cell counter, Biosensors and Bioelectronics, vol. 57, pp. 48-53, 2014.
Lind et al., The density difference between tissue and neural probes is a key factor for glial scarring, Scienific Reports, vol. 3, 7 pages, 2013.
Liou, High sensitivity magnetoresistive sensors for both DC and EMI magnetic field mapping, University of Nebraska, SERDP Project MR-1716, 19 pages, 2012.
Lorach et al., Neural stimulation for visual rehabilitation: advances and challenges, Journal of Physiology, pp. 421-431, 2013.
Love et al., Diamond like carbon coatings for potential application in biological implants—a review, Tribology International, vol. 63, pp. 141-150, 2013.
Lyle et al., Direct communication between magnetic tunnel junctions for nonvolatile logic fan-out architecture, Applied Physics Letters, vol. 97, pp. 152504-1-152504-3, 2010.
Malmivuo, Comparison of the properties of EEG and MEG in detecting the electric activity of the brain, Brain Topogr, vol. 25, pp. 1-19, 2012.
Maynard et al., The Utah intracortical electrode array: a recording structure for potential brain-computer interfaces, Electroencephalography and Clinical Neurophysiology, Vo. 102, pp. 228-239, 1997.
Medtronic, http://www.medtronic.com/innovation/smarter-dbs.html#sthash.D7onn0eo.dpuf, accessed 2016.
Metz et al., Flexible polyimide probes with microelectrodes and embedded microfluidic channels for simultaneous drug delivery and multi-channel monitoring of bioelectric activity, Biosensors and Bioelectronics, vol. 19, pp. 1309-1318, 2004.
Normann et al., A neural interface for a cortical vision prosthesis, Vision Research vol. 39, pp. 2577-2587, 1999.
Ordonez et al., Improved polyimide thin-film electrodes for neural implants, 34th Annual International Conference of the IEEE, pp. 5134-5137, 2012.
Parkin et al., Magnetic domain-wall racetrack memory, Science, vol. 320, pp. 190-194, 2008.
Parkinson, http://www.parkinson.org/, accessed 2016.
Pearce et al., Microtechnology, Meet neurobiology, Critical Review, The Royal Society of Chemistry, Lab Chip vol. 7, pp. 30-40, 2007.
Malmivuo, Bioelectromagnetism: Principles and Applications of Bioelectric and Biomagnetic Fields, Oxford University Press, pp. 33-463, 1995.
Roth et al., The Magnetic Field of a Single Axon—A Comparison of Theory and Experiment, Journal of Biophysics, vol. 48, pp. 93-109, 1985.

\* cited by examiner

MAGNETIC NANOSTIMULATOR AND NANOSENSOR ARRAY FOR BIOLOGICAL MATERIAL STIMULATION AND SENSING

CROSS-REFERENCE TO RELATED APPLICATION

The present application is based on and claims the benefit of U.S. Provisional patent applications Ser. No. 62/148,053, filed Apr. 15, 2015 and Ser. No. 62/148,465, filed Apr. 16, 2015, the content of which is hereby incorporated by reference in its entirety.

BACKGROUND

By applying a voltage or a changing magnetic field to a nerve cell, it is possible to cause the nerve cell to "fire" during which the nerve cell depolarizes and then repolarizes.

In external magnetic stimulation, a strong alternating magnetic field is generated external to the body and is directed into the body. Within the body, the fluctuating magnetic field creates a current along the nerve cells that cause the cells to fire.

Such external systems require strong magnetic fields in order to penetrate into the body. However, as the magnetic fields increase in strength, the area affected by the magnetic fields also increases resulting in low resolution stimulus of the nerve cells. As a result, it is difficult to direct the external magnetic field to only a select number of nerve cells.

In deep brain stimulation, an electrode is inserted into the body and an electric field is generated in the target area to be stimulated. This electric field causes nerve cells to fire.

SUMMARY

An apparatus includes a substrate and a plurality of biological material stimulators positioned on the substrate. Each biological material stimulator forms a fluctuating magnetic field capable of inducing a current in biological material.

In accordance with a further embodiment, a method includes introducing an array of biological material stimulators mounted on a substrate into a living body and applying signals to the array of biological material stimulators to cause the biological material stimulators to generate a fluctuating magnetic field that induces a current in biological material surrounding the biological material stimulator.

A neuron stimulator includes a substrate having an outer surface and a magnetic nanowire extending transverse to the outer surface such that a top of the nanowire is above the substrate. The magnetic nanowire has at least two magnetic domains with at least one moveable domain wall between the magnetic domains.

DETAILED DESCRIPTION

Embodiments described below provide arrays of magnetic nanostructures that generate and/or use magnetic fields for biomedical applications. For example, some magnetic nanostructures are be used to modulate (stimulate) biological material such as cells, tissue and organs while other magnetic nanostructures used to sense cellular activity. The magnetic nanostructures can include structures such as nanowires, magnetic tunnel junctions or giant magnetoresistance elements, for example. For embodiments that use nanowires, domain walls are introduced into a nanowire and are moved through the nanowire thereby creating a fluctuating magnetic field external to the nanowire. In accordance with some embodiments, the nanowires are formed as vertical half-loops or bridges that extend away from a substrate so as to place the nanowires in closer contact with the cells that they are stimulating. In accordance with some embodiments, half loops and bridges of differing heights are used to improve contact with the biological material. For embodiments that use magnetic tunnel junctions or giant magnetoresistance elements as the nanostructures, the magnetic tunnel junction or the giant magnetoresistance elements are raised relative to the substrate to provide better contact between the elements and the cells they are to stimulate. The magnetic domain of the top-most magnetic layer in the magnetic tunnel junction or the giant magnetoresistance element is then rotated based on an input signal to form a low frequency magnetic field around the magnetic tunnel junction or giant magnetoresistance element. The magnetic field generated by the magnetic nanostructures can be controlled by either an electrical signal or by a light signal.

In accordance with some embodiments, the magnetic nanostructures are mounted on a flexible substrate such that the substrate and the magnetic nanostructures can be wrapped around biological material to thereby better focus the stimulation signals onto a particular area in the body, such as a particular area in the brain.

Figure 1:
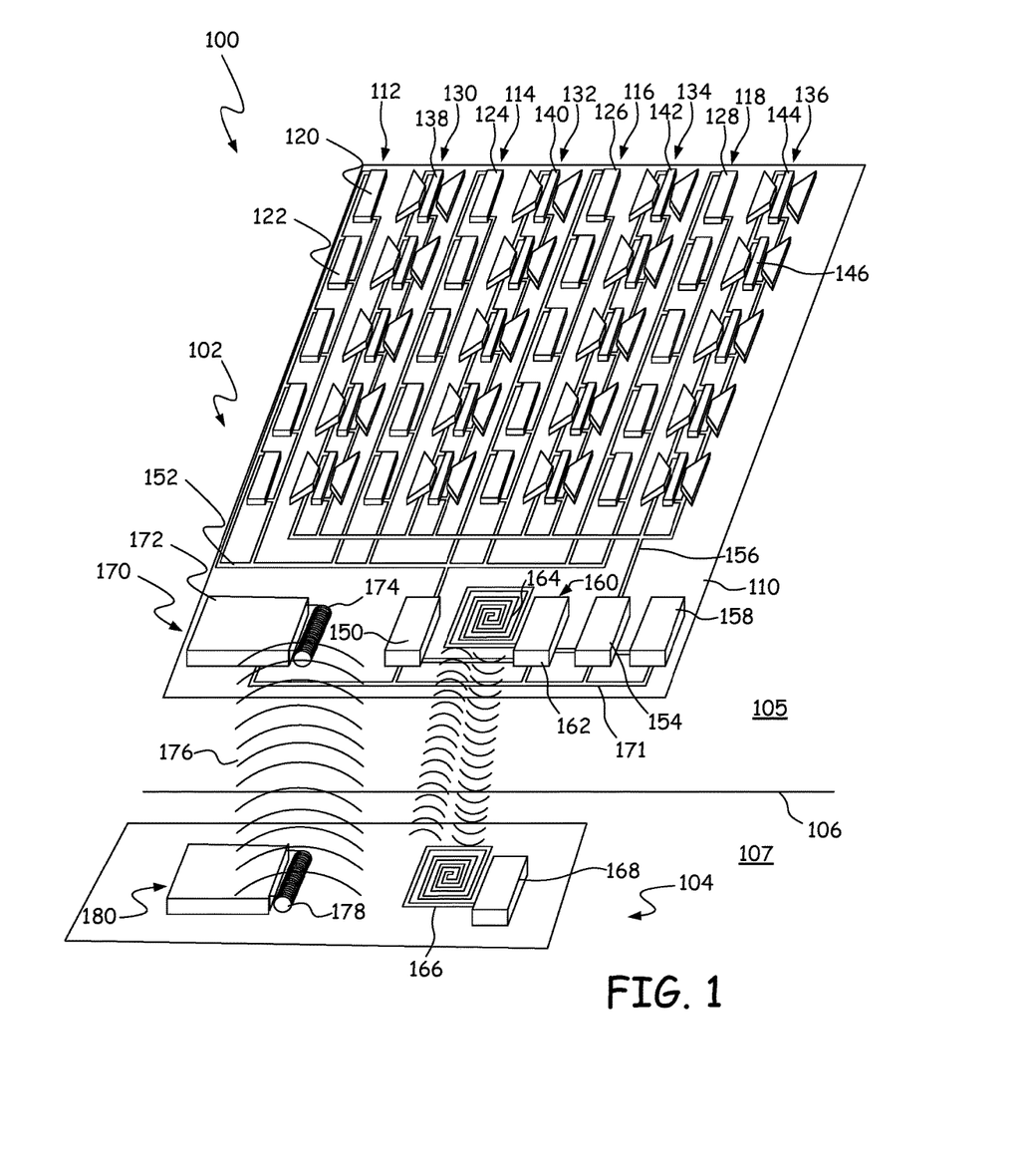
FIG. 1 is a schematic diagram of a nanostimulation/nanosensing system in accordance with one embodiment.

FIG. 1 is a schematic diagram of a nanostimulation/nanosensor system 100 including an implanted device 102 and an external device 104. Implanted device 102 is located within a living body 105 and external device 104 is located in an environment 107 exterior to living body 105 and separated from living body 105 by an outer surface 106 of the living body. In accordance with one embodiment, implanted device 102 is inserted into living body 105 through an incision in outer surface 106 and then the incision is sealed such that there is no wired connection between implanted device 102 and external device 104.

Implanted device 102 includes a flexible substrate 110 having a plurality of nanostimulators and nanosensors mounted thereon. In accordance with one embodiment, the plurality of nanostimulators and nanosensors are arranged in an array. In FIG. 1, there are four columns 112, 114, 116 and 118 of nanostimulators, such as nanostimulators 120, 122, 124, 126 and 128. There are also four columns of nanosensors 130, 132, 134 and 136 that include nanosensors, such as nanosensors 138, 140, 142, 144 and 146.

Each nanostimulator generates a fluctuating magnetic field when active that interacts with biological material. Although these interactions can include interfering with the normal operation of the biological material, changing the physical structure of the biological material, changing the operation of the biological material and stimulating the biological material to generate a response from the biological material, for example, the interactions are referred to generically as stimulating the biological materials and the devices used to generate the fluctuating magnetic fields are referred to generically as stimulators. In the descriptions herein, the reference to stimulating should be read to include all interactions between the magnetic field generating devices and the biological tissue and the references to stimulators and nanostimulators should be read to include all implanted devices that generate a fluctuating magnetic field that interacts with biological tissue.

In addition to the nanostimulators and nanosensors, a stimulator controller 150, a sensor controller 154, a memory 158, a communication circuit 160 and a power circuit 170 are mounted on flexible substrate 110. The nanostimulators are connected to stimulator controller 150 by a stimulation bus 152 on flexible substrate 110 to allow controller 150 to activate individual nanostimulators at any one time and to activate multiple nanostimulators at the same time. The stimulator nanostructures such as the nanowire, mtj and giant magnetoresistance nanostructure can be controlled by applying electrical signals to stimulation bus 152 or by applying light signals to stimulation bus 152. In embodiments where light is used to control the stimulators, stimulation bus 152 takes the form of optic wave guides.

Similarly, the nanosensors are connected to sensor controller 154 by a sense control bus 156 that allows the sensor controller 154 to receive a sensed value from each of the nanosensors. Sensor controller 154 can store the sensed values in memory 158. In addition, sensor controller 154 can transmit the sensed values or the values stored in memory 158 wirelessly using communication circuit 160, which consists of a wireless communication controller 162 and an antenna 164. Wireless communication controller 162 communicates through antenna 164 to an antenna 166 that is coupled to a wireless communication circuit 168 of external device 104. Through this communication, sensor controller 154 is able to communicate the sensed values externally where the sense values may be used by an external processor.

Stimulator controller 150 may receive instructions to stimulate particular nanostimulators through communication circuit 160. In particular, instructions may pass through wireless communication circuit 168 and antenna 166 and be received by antenna 164 and wireless communication controller 162 before being provided to stimulator controller 150.

Although communication circuit 160 is shown to be wireless in FIG. 1, in other embodiments, a wired connection is provided between implanted device 102 and external device 104.

Power circuit 170 provides power to sensor controller 150, stimulator controller 154, communication circuit 160 and memory 158 through a power bus 171. Some of the power provided to stimulator controller 150 is routed to the nanostimulators by sensor controller 150 to cause the nanostimulators to generate a low frequency magnetic field as discussed further below. Some of the power provided to sensor controller 154 is routed to the nanosensors to read a magnetic field value sensed by the nanosensors as discussed further below.

In accordance with one embodiment, power source 170 includes an induction loop 174 that generates an electrical current when it receives an alternating magnetic field 176. The current from induction loop 174 can be used to provide power to power bus 171 directly or can be used to recharge a battery 172 that in turn provides power to power bus 171. In accordance with one embodiment, the alternating magnetic field 176 received by induction loop 174 is generated by a corresponding induction loop 178 in a power system 180 of external device 104. Thus, external device 104 provides power wirelessly to implanted device 102. This power can be provided periodically to charge battery 172 or can be provided continuously to directly power the components of implanted device 102. After battery 172 has been charged, external device 104 can be removed and does not need to be present in order for implanted device 102 to operate since battery 172 can provide power while external device 104 is not present. In accordance with other embodiments, a wired connection between implanted device 102 and external device 104 allows power to be conveyed between external device 104 and implanted device 102 either periodically to recharge battery 172 or continuously to power implanted device 102.

Figure 2:
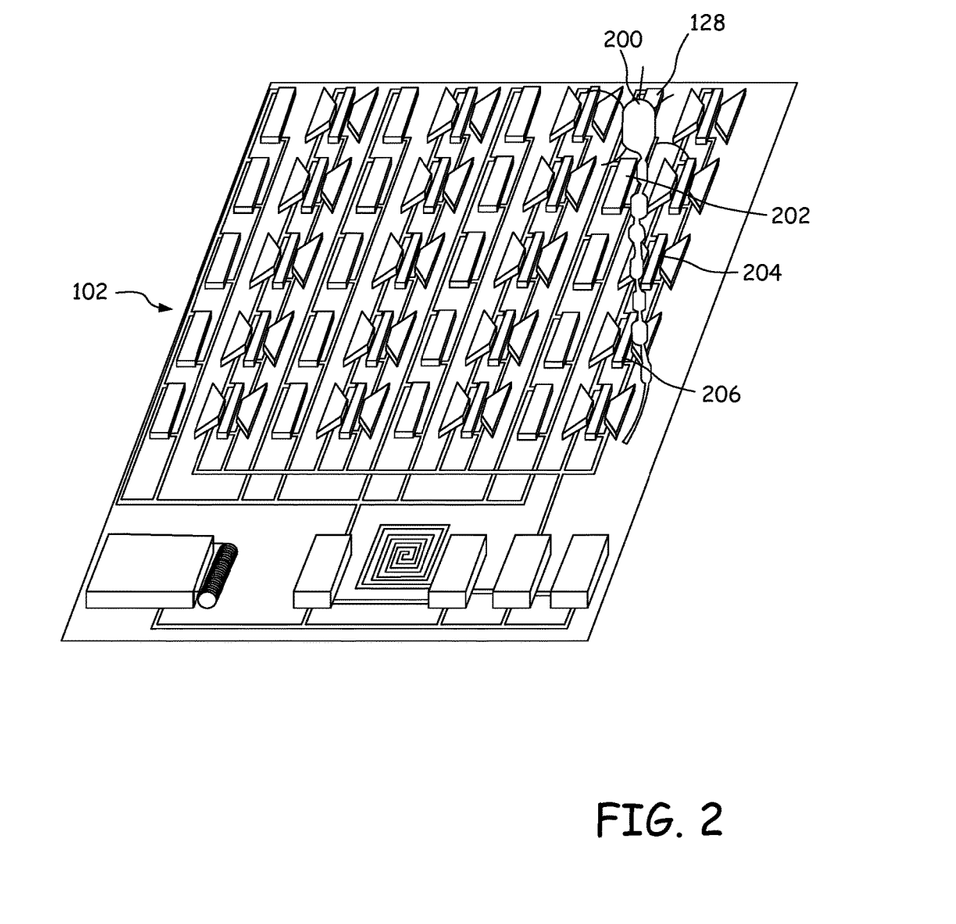
FIG. 2 is a perspective view of the implanted device of FIG. 1 next to a neuron.

FIG. 2 shows implanted device 102 in contact with a neuron 200. In particular, two nanostimulators 128 and 202 are in contact with neuron 200 and two nanosensors 204 and 206 are in contact with neuron 200. As a result, one or both of nanostimulators 128 and 202 may stimulate neuron 200 to cause it to fire while one or both of nanosensors 204 and 206 may sense the firing of neuron 200 by sensing the magnetic field generated by neuron 200 as current passes through neuron 200. Although direct contact with the neuron is not required to stimulate the neuron or to sense a firing event in the neuron, contact does improve the ability to stimulate the neuron and sense a firing event in the neuron.

Figure 3:
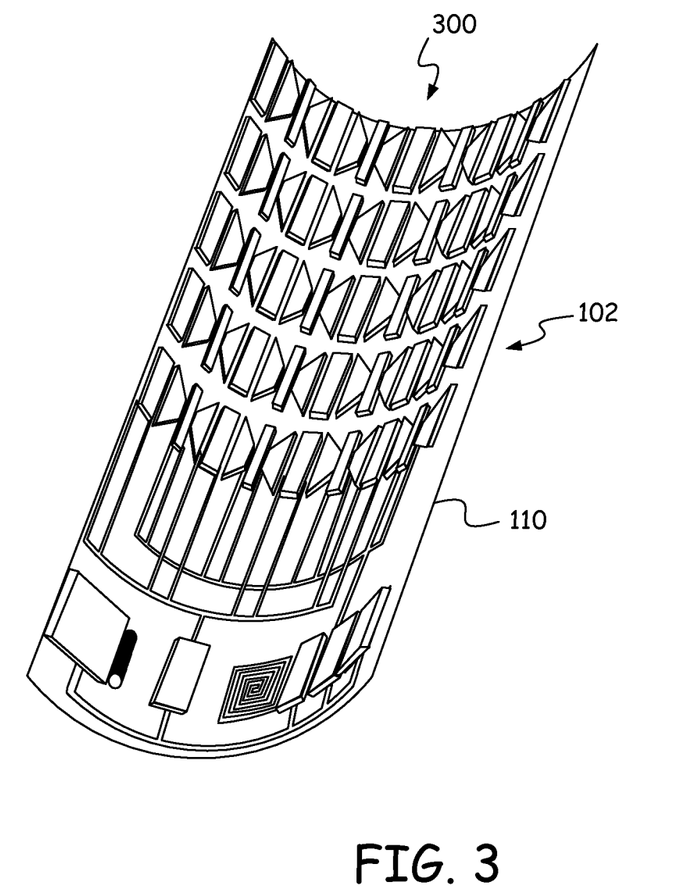
FIG. 3 is a perspective view of the implanted device of FIG. 1 in a bent configuration.

As mentioned above, the substrate 110 of implanted device 102 is flexible as shown in FIG. 3. Thus, implanted device 102 can be bent to form a curved shape 300 such that implanted device 102 can be wrapped around biological material to thereby focus the stimulation to a particular area in the body and to focus the sensing of cellular activity in a particular area of the body. Although flexible substrate 110 is shown flexed along a first axis, flexible substrate 110 is bendable along multiple axes.

Although FIGS. 1-3 show a combination of nanosensors and nanostimulators on implanted device 102, in other embodiments, the implanted device contains only nanostimulators and in other embodiments, the implanted device contains only nanosensors. In addition, although the nanosensors and nanostimulators of FIGS. 1-3 are shown in separate columns, in other embodiments, nanosensors and nanostimulators are in a same column.

Figure 4:
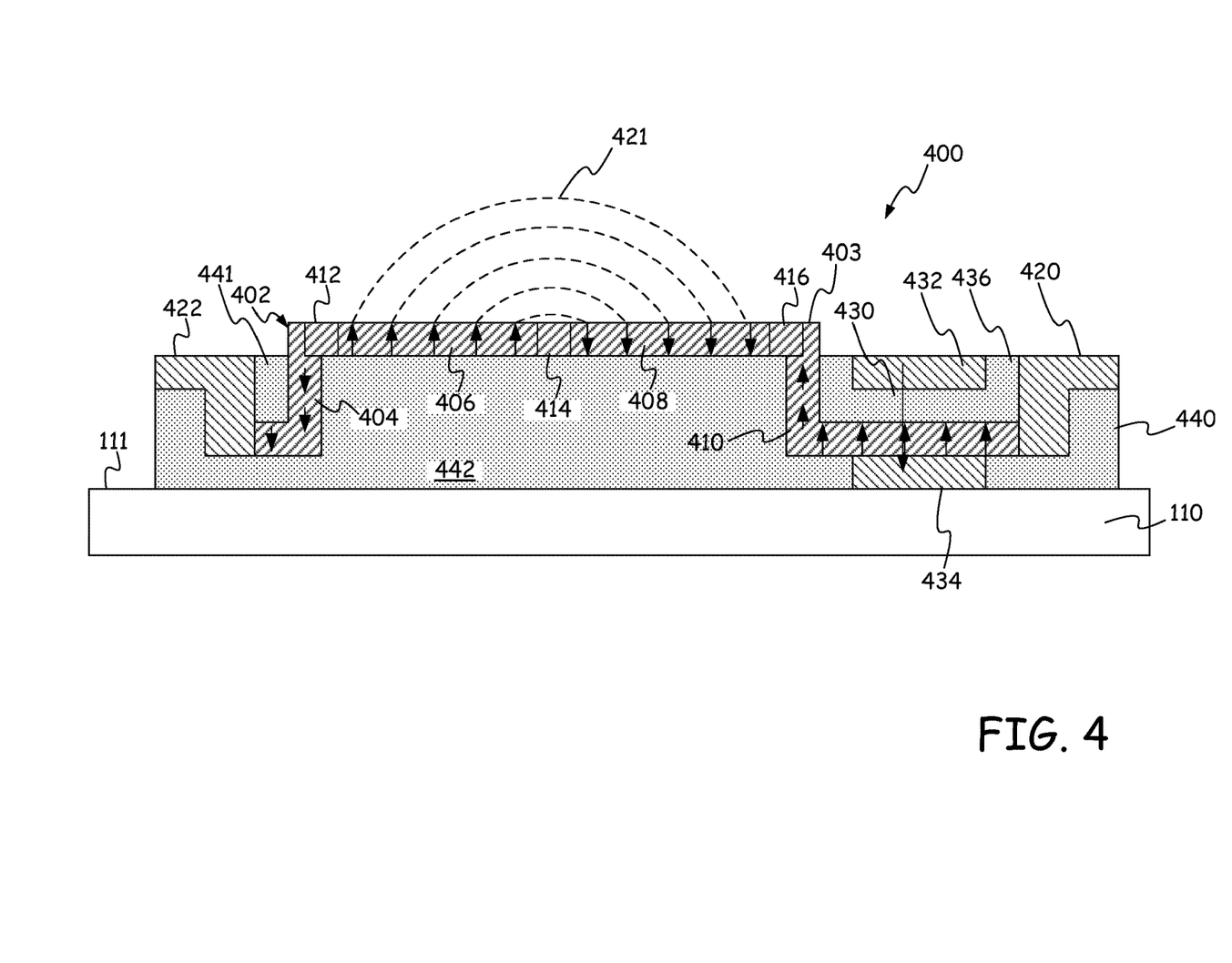
FIG. 4 is a sectional side view of a nanowire stimulator in accordance with one embodiment.

FIG. 4 provides a sectional side view of a nanostimulator 400, which can be used as one of the nanostimulators such as nanostimulator 120 of FIG. 1. Nanostimulator 400 uses a nanowire 402 that includes a plurality of magnetic domains 404, 406, 408 and 410 with neighboring domains being separated by domain walls 412, 414 and 416. In accordance with one embodiment, nanowire 402 is constructed of CoFeB. Nanowire 402 includes two ends, which are in contact with two respective electrical contacts 420 and 422. By passing a polarized current between electrical contacts 420 and 422 through nanowire 402, it is possible to move domain walls 412, 414 and 416 and thereby change the magnetic field 421 generated by nanowire 402. This change in magnetic field 421 creates a fluctuating magnetic field that interacts with biological material. In the case of neurons, the fluctuating magnetic field can induce depolarization in a neuron, causing the neuron to fire. In other biological materials, the fluctuating magnetic field can cause the material or the material's function to be altered in some way.

To change the direction of the magnetic domain in nanowire 402, a current 430 can be passed from contact 432 to contact 434 to generate a magnetic field in nanowire 402 sufficient to set the direction of the magnetic domain.

The structures of nano stimulator 400 are formed through photolithography and milling on top of an outer surface 111 of flexible substrate 110. As a result, nanowire 402 extends transverse to outer surface 111 such that a top 403 of nanowire 402 is above substrate 110. To isolate the electrical contacts, layers of insulating material 436, 440, 441 and 442 are deposited and milled.

Figure 5:
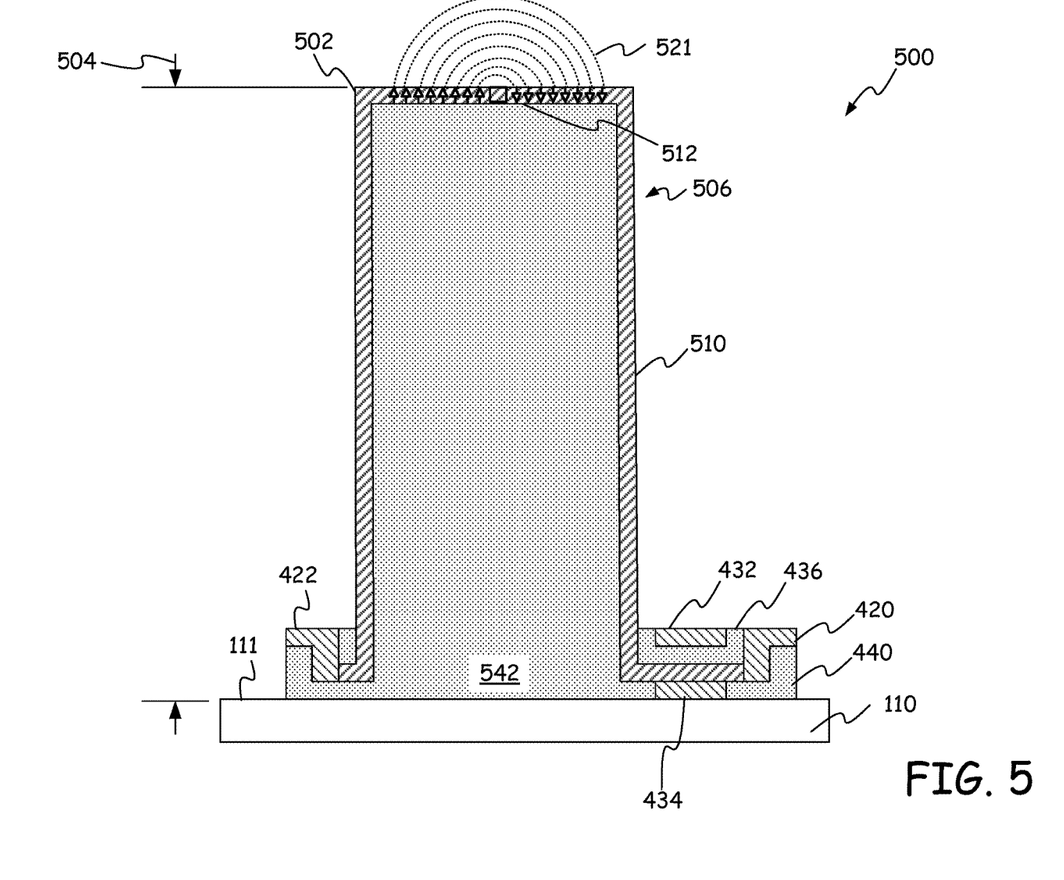
FIG. 5 is a sectional side view of a nanowire bridge stimulator in accordance with one embodiment.

FIG. 5 provides a sectional side view of a nanostimulator 500, which is similar to the nanostimulator 400 of FIG. 4 except that nanowire 402 has been replaced with nanowire 502, which has a greater height 504 than nanowire 402. Nanowire 502 contains magnetic domains pointing in different directions and separated by domain walls so as to produce a magnetic field 521 that fluctuates as the domain walls are moved through nanowire 502 by a current passing through nanowire 502 from contact 420 to contact 422. Additional domain walls may be added to nanowire 502 by applying a current between contacts 432 and 434.

Figure 6:
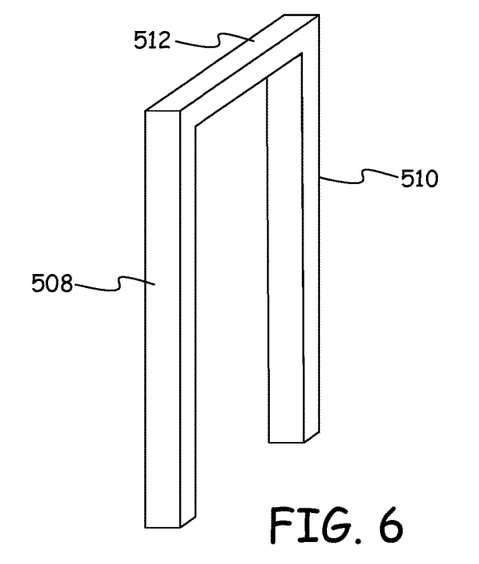
FIG. 6 is a perspective view of the nanowire bridge stimulator of FIG. 5.

Nanowire 502 forms a bridge structure 506 having legs 508 and 510 and a cross beam 512. Legs 508 and 510 extend transverse to outer surface 111 of substrate 110 such that the top of cross beam 512 is above substrate 110. In FIG. 5, bridge 506 is filled with insulating material 542. In other embodiments, insulating material 542 is not present and the interior of bridge 506 is empty as shown in the perspective view of FIG. 6.

In embodiments which use bridge structure 506 as the nanostimulator, different nanostimulators can have different heights 504 within implantable device 102. Thus, the nanostimulators in columns 112, 114, 116 and 118 can each be at a different height allowing for differing levels of physical contact between the nanostimulators and the surrounding biological material.

Figure 7:
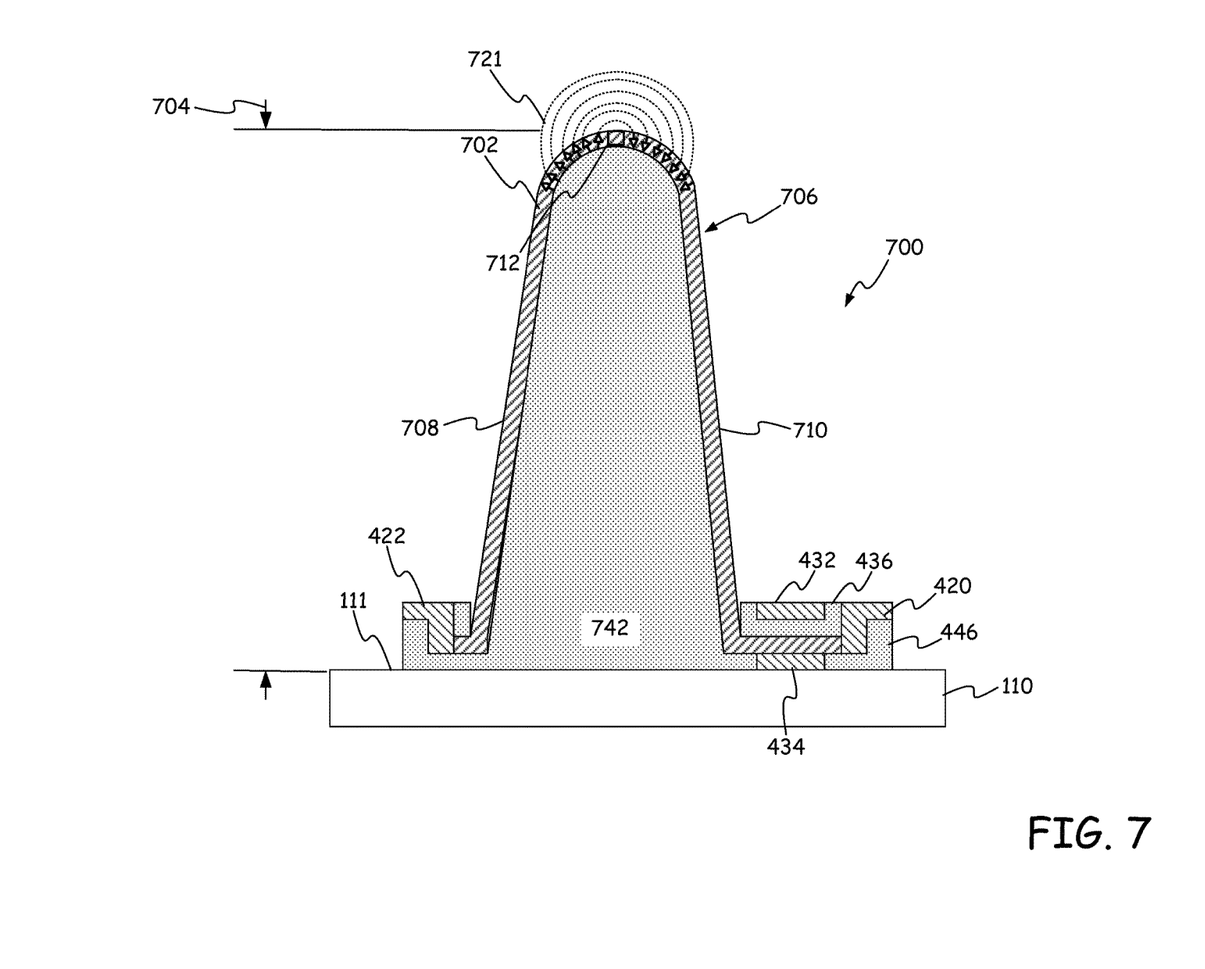
FIG. 7 is a section side view of a nanowire half loop stimulator in accordance with one embodiment.

FIG. 7 provides a sectional side view of a further embodiment of a nanostimulator in the form of a half looped nanowire 702. Nanowire 702 contains magnetic domains pointing in different directions and separated by domain walls similar to the domains and domain walls of nanowire 402 of FIG. 4. The different domains form a magnetic field 721 that fluctuates as the domain walls are moved by current passing from contact 420 to contact 422. Additional domain walls may be added to nanowire 702 by applying a current between contacts 432 and 434. Nanowire 702 is formed into a half loop 706 with a rounded top 712 and two legs 708 and 710. Half loop 706 extends transverse to substrate 110 to a height 704 above outer surface 111 of flexible substrate 110. In accordance with one embodiment, implantable device 102 includes multiple half loop nanostimulators, such as shown in FIG. 7, each with a different height 704, such that the implantable device 102 has an array of half loop nanostimulators each at different heights.

Figure 8:
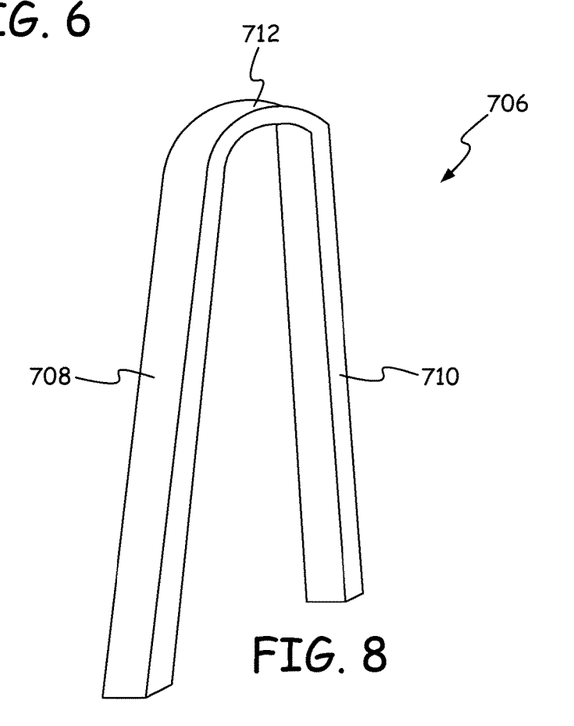
FIG. 8 is a perspective view of the nanowire half loop stimulator of FIG. 7.

In FIG. 7, the interior of half loop 706 is filled with an insulating material 742. In other embodiments, insulting material 742 does not fill half loop 706. Instead, an empty space is present within half loop 706 as shown in the perspective view of half loop 706 shown in FIG. 8.

The magnetic stimulation of neurons using the various embodiments causes a neuron to "fire". Before firing, the neuron membrane has a resting potential of −70 mv. At the beginning of the firing event, a current of K+ ions flows into the membrane causing the membrane potential to rise to 30 mv. This rise in the membrane's potential is referred to as depolarization. A current of K+ ions then flows out of the membrane causing repolarization followed by hyperpolarization. The membrane then returns to its resting potential.

The amount of magnetic flux required to create depolarization can be calculated using Ampere's law:

$$\oint \vec{B} \cdot \vec{dl} = \mu_0 I = \mu_0 \oint \sigma \vec{E} \cdot \vec{dA}$$

For a typical neuron: σ=0.33 s/m and E=100 V/m. If the stimulator is placed a distance 10 μm, then the required magnetic field strength to cause depolarization of the neuron is B=20 nT.

Domain walls generate magnetic fields external to the magnetic material. For example, a rectangular portion of a domain wall will produce an external magnetic field at a position x, y, z from the center of the rectangle of:

$$B_x = \frac{\mu_0 M_s t}{2\pi s} \log \left[ \frac{(s-2y) + \sqrt{(2x-w)^2 + (2y-s)^2 + 4z^2}}{(s-2y) + \sqrt{(2x+w)^2 + (2y-s)^2 + 4z^2}} \cdot \frac{(-s-2y) + \sqrt{(2x+w)^2 + (2y+s)^2 + 4z^2}}{(-s-2y) + \sqrt{(2x-w)^2 + (2y-s)^2 + 4z^2}} \right]$$

$$B_y = \frac{\mu_0 M_s t}{2\pi s} \log \left[ \frac{(w-2x) + \sqrt{(2x-w)^2 + (2y-s)^2 + 4z^2}}{(w-2x) + \sqrt{(2x+w)^2 + (2y+s)^2 + 4z^2}} \cdot \frac{(-w-2x) + \sqrt{(2x+w)^2 + (2y+s)^2 + 4z^2}}{(-w-2x) + \sqrt{(2x+w)^2 + (2y-s)^2 + 4z^2}} \right]$$

$$B_z = \frac{\mu_0 M_s t}{2\pi s} \left\{ \tan^{-1} \left[ \frac{2(w/2-x)(s/2-y)}{z\sqrt{(2x-w)^2 + (2y-s)^2 + 4z^2}} \right] + \tan^{-1} \left[ \frac{2(w/2-x)(s/2+y)}{z\sqrt{(2x-w)^2 + (2y+s)^2 + 4z^2}} \right] - \tan^{-1} \left[ \frac{2(-w/2-x)(s/2-y)}{z\sqrt{(2x+w)^2 + (2y-s)^2 + 4z^2}} \right] - \tan^{-1} \left[ \frac{2(-w/2-x)(s/2+y)}{z\sqrt{(2x+w)^2 + (2y+s)^2 + 4z^2}} \right] \right\}$$

where $M_s$ is the saturation magnetization of the material, $\mu_0$ is the permeability of the material, w is the width of the magnetic material, t is the thickness of the magnetic material, and s is the width of the domain wall transverse to w and t.

In a further embodiment, a triangle model of a transverse domain wall is used to determine the magnetic field at positions/external to the transverse domain wall. The triangle is an isosceles triangle with its base equal to the width of the domain wall and its height equal to the width of the magnetic material. To determine the magnetic field, the triangle broken into rectangles and the fields from the rectangles are summed to form the field for the domain wall.

In order to generate a current along the axis of the neuron, the magnetic field produced by the domain wall must fluctuate. To produce this fluctuation, several embodiments move the domain wall through the material. For a magnetic nanowire, a domain wall can be moved by passing a spin polarized current through the nanowire.

The use of transverse domain walls instead of current carrying loops was selected by the present inventors for power efficiency and to avoid damaging neurons. Under electrical deep brain stimulation, 1-4 Volts of electrical energy is applied to the subthalamic nucleus (STN) to trigger the neuron. From Faraday's law of electromagnetic induction, the amount of magnetic field required to induce 1 V EMF for the stimulation of the STN is 800 Gauss (with a radius of STN 2 mm and a pulse width 1 μs). To generate 800 Gauss magnetic field from current carrying wire, a large current of 3-50 Amps would have to be applied to the wire. This would require a great deal of power and would generate a substantial amount of heat that may damage the neurons. The field from one moving transverse domain wall is sufficient to stimulate the STN. In addition, the domain wall is moved by using a very small alternating current of around 74 micro-Amps. The alternating current supplied to a magnetic layer produces spin-transfer torque which induces motion of domain wall. The spin-transfer torque combined with spin-orbit torque reduces significantly the amount of current required to move the domain wall.

Figure 9:
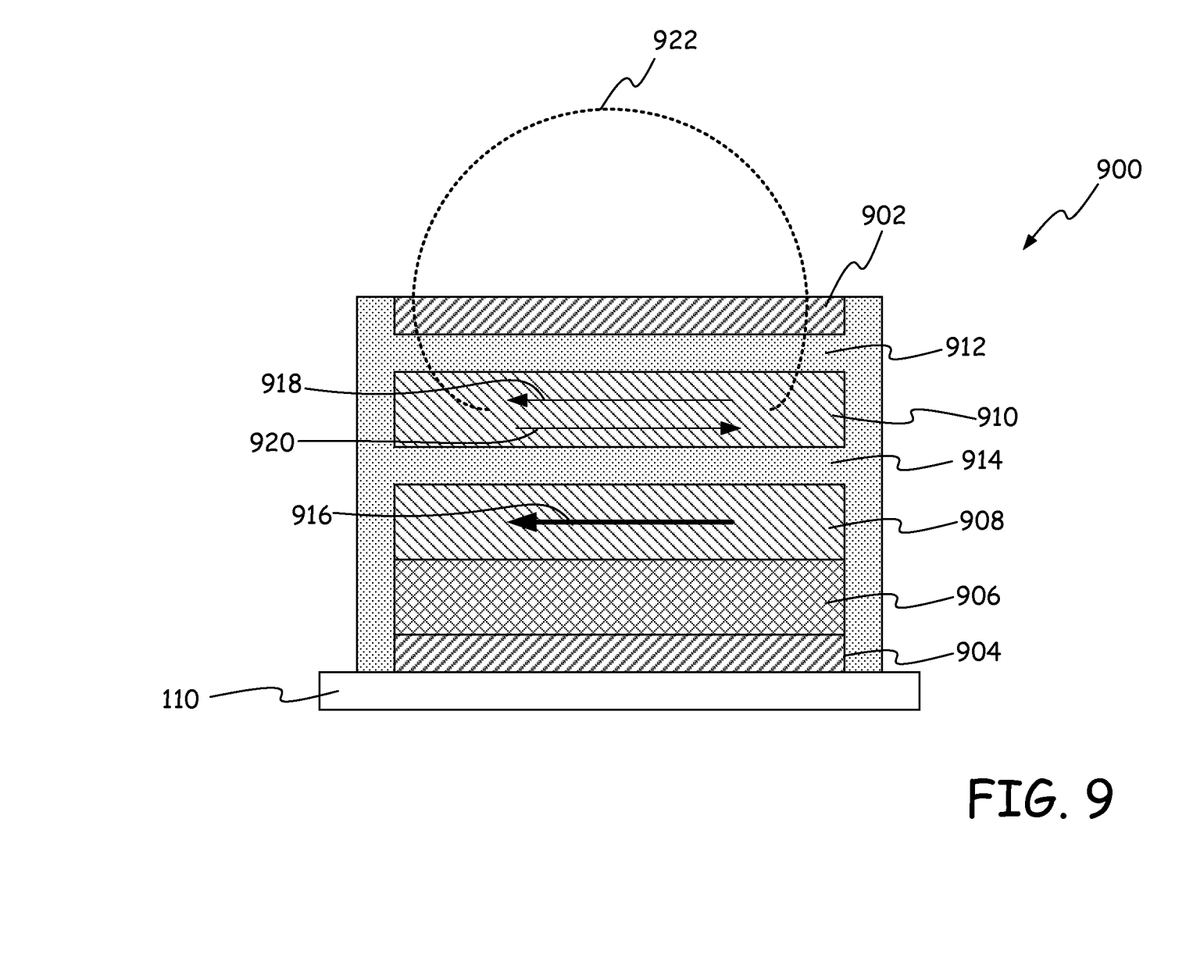
FIG. 9 is a sectional side view of a Magnetic Tunnel Junction (MTJ) nanostimulator in accordance with one embodiment.

FIG. 9 provides a sectional view of a nanostimulator 900 in accordance with a further embodiment. Nanostimulator 900 is formed of a magnetic tunnel junction nanostructure that includes two electrical contacts 902 and 904, an anti-ferromagnetic layer 906, a fixed or pinned ferromagnetic layer 908, a free magnetic layer 910 and insulating layers 912 and 914. Fixed magnetic layer 908 has a magnetic domain with a dipole direction 916 that is fixed while free magnetic layer 910 has a magnetic domain with a dipole direction that can be switched by applying spin polarized current between contacts 902 and 904. Spin polarized current in a first direction causes the magnetic domain to point in a first direction 918 and spin polarized current in a second direction causes the magnetic domain to point in a second direction 920. Free magnetic layer 910 generates an external magnetic field 922 that can interact with biological material. By alternating between directions 918 and 920 through the application of the spin polarized current, it is possible to create a low frequency fluctuating magnetic field 922 that can interact with biological material such as cells, tissues and organs, for example. In accordance with other embodiments, a giant magneto resistive nanostructure is used in place of the magnetic tunnel junction nanostructure.

Figure 10:
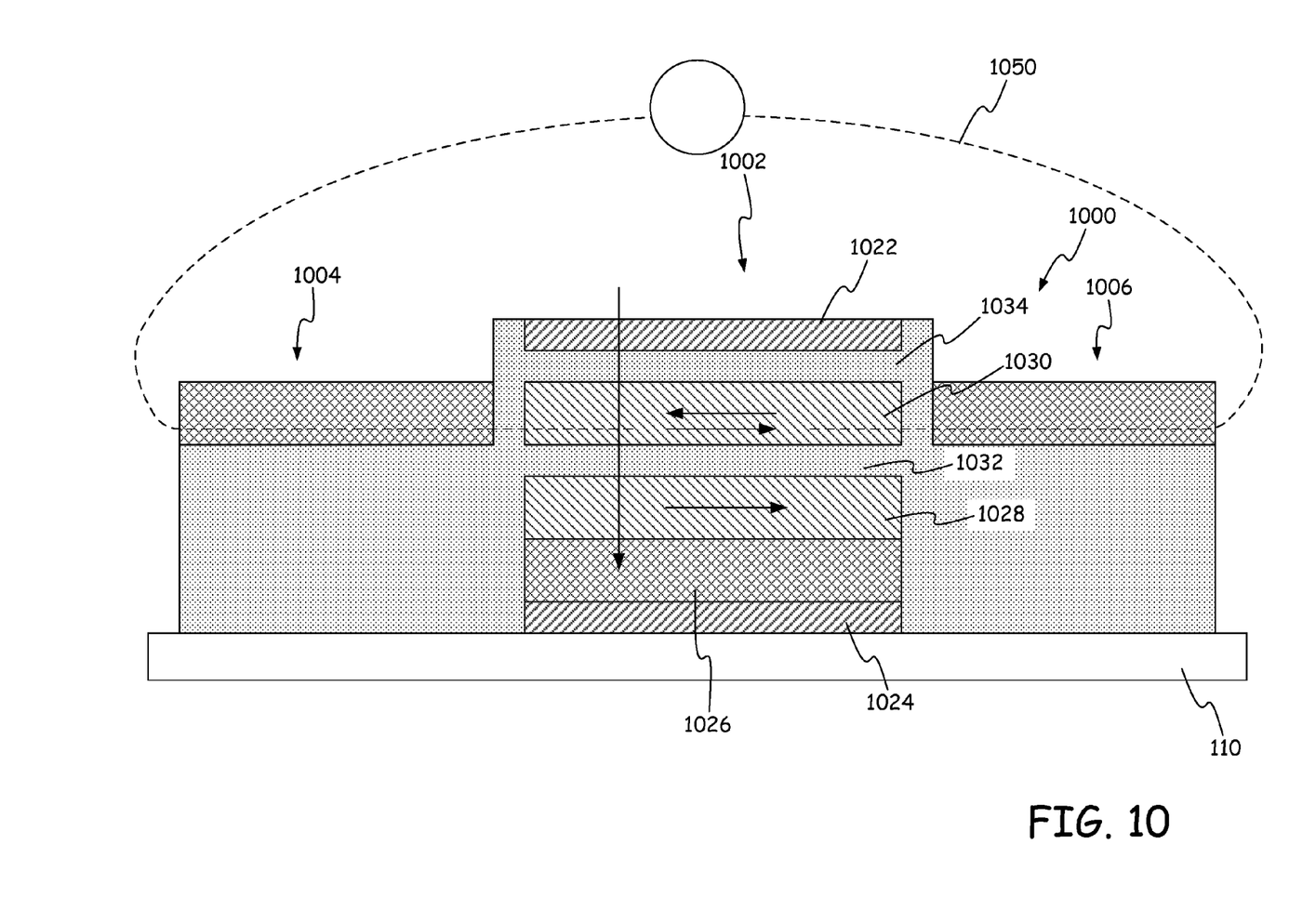
FIG. 10 is a section side view of a Magnetic Tunnel Junction (MTJ) nanosensor in accordance with one embodiment.
Figure 11:
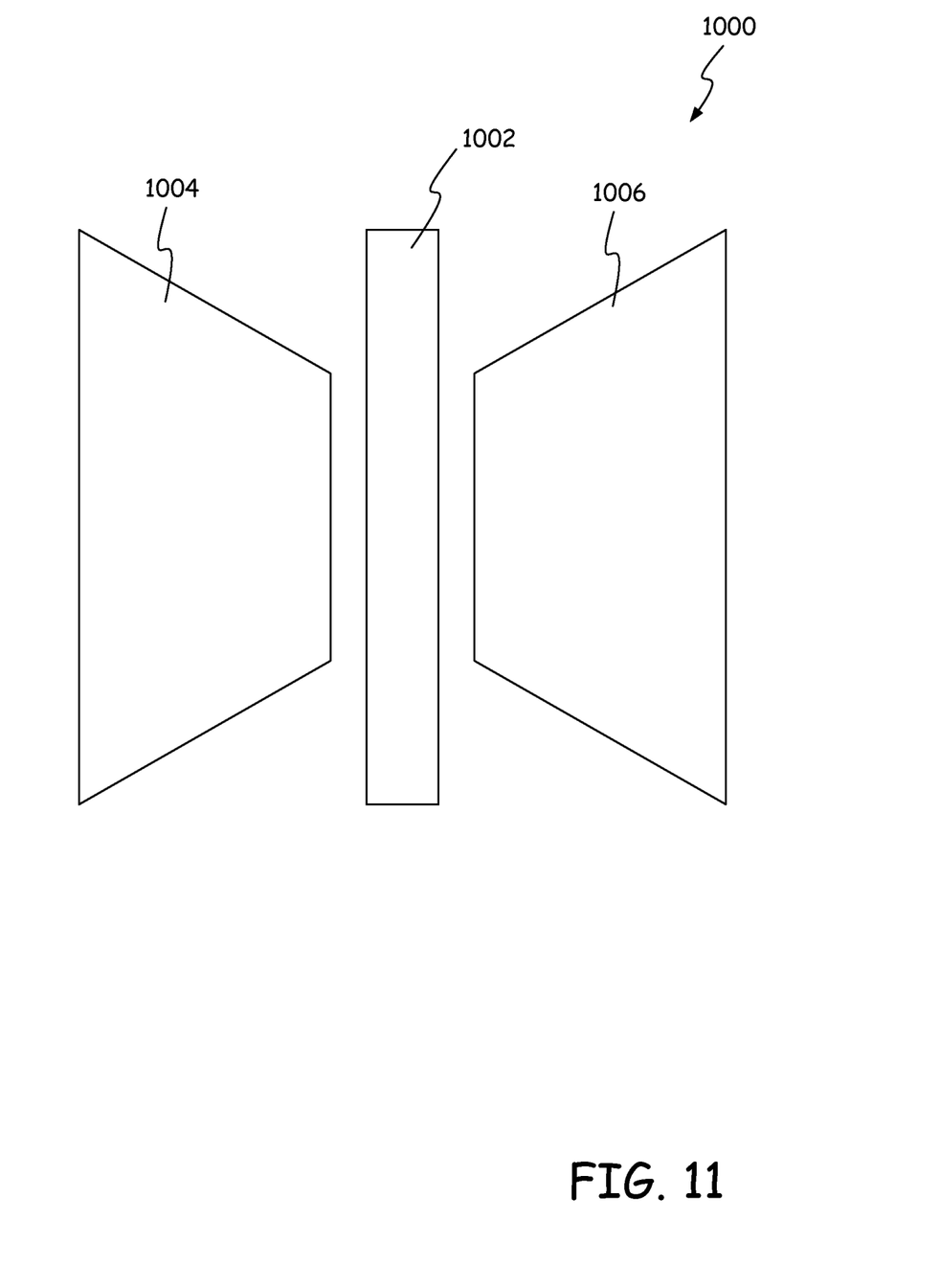
FIG. 11 is a top view of the MTJ nanosensor of FIG. 10.

FIG. 10 provides a side sectional view and FIG. 11 provides a top view of a magnetic nanosensor 1000 that can be used as one of the nanosensors on an implanted device 102, such as nanosensor 138. Nanosensor 1000 includes a central sensing portion 1002 and two magnetic flux guides 1004 and 1006. Flux guides 1004 and 1006 concentrate magnetic flux into a smaller area within central sensing portion 1002 to thereby increase the sensitivity of central sensing portion 1002.

Central sensing portion 1002 is constructed of a magnetic tunnel junction similar to the magnetic tunnel junction of stimulator 900 of FIG. 9. In particular, the magnetic tunnel junction of nanosensor 1000 includes electrical contacts 1022 and 1024, non-ferromagnetic layer 1026, pinned magnetic layer 1028, free magnetic layer 1030 and insulator layers 1032 and 1034. Pinned magnetic layer 1028 has a fixed domain direction and free magnetic layer 1030 has a free domain direction that may be set based on an external magnetic field 1050 generated by the firing of a neuron or other living biological material. The direction of the domain of free magnetic layer 1030 can be determined by passing a current between electrical contacts 1022 and 1024. When the domain of free magnetic layer 1030 is parallel to pinned magnetic layer 1028, a first resistance is detected and when the domain of free magnetic layer 1030 is antiparallel to the domain direction of pinned magnetic layer 1028 a second resistance is detected. Thus, by measuring this resistance, it is possible to determine the direction of external magnetic field 1050 and thus it is possible to determine if a neuron has fired.

Nanosensor 1000 may be used alone to sense neuron firing events or may be included as part of a Wheatstone bridge to sense firing events. For example, nanosensor 1000 can be used as part of Wheatstone bridge 1200 of FIG. 12. In Wheatstone bridge 1200, three magnetic tunnel junctions 1202, 1204 and 1206 are used in cooperation with magnetic tunnel junction nanosensor 1000. Magnetic tunnel junction 1202, 1204 and 1206 are protected from external magnetic fields by a shielding layer and therefore their free layer does not change its domain direction and therefore does not change its resistance.

Figure 12:
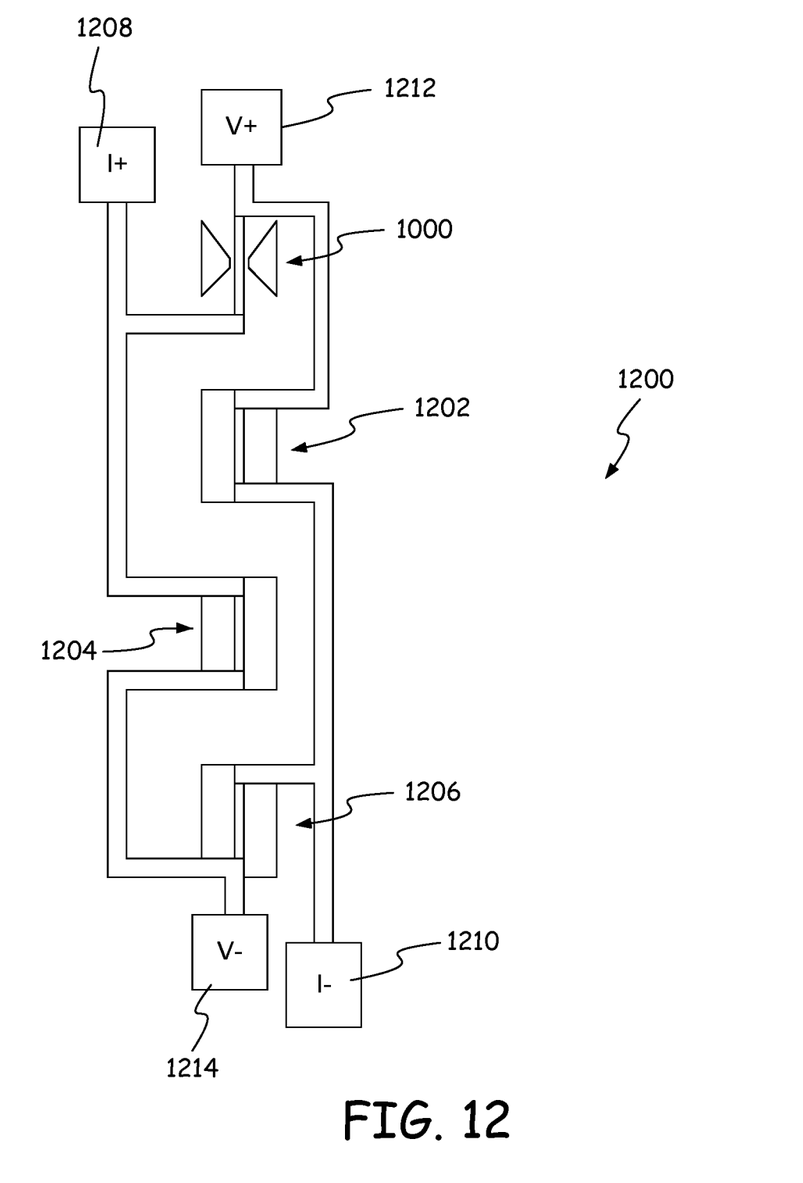
FIG. 12 is a top view of a Wheatstone Bridge nanosensor in accordance with one embodiment.

A current is passed between current contacts 1208 and 1210 along two parallel paths. A first path is through nanosensor 1000 and magnetic tunnel junction 1202 and a second path is through magnetic tunnel junction 1204 and magnetic tunnel junction 1206. When the external magnetic field sensed by nanosensor 1000 is in a first direction it causes the domain of the free layer of nanosensor 1000 to be in a first direction and nanosensor 1000 to have a first resistance. This first resistance is balanced by Wheatstone bridge 1200 such that a voltage between voltage contacts 1212 and 1214 is zero. When the magnetic field changes directions thereby changing the domain direction of the free layer of nanosensor 1000, the resistance of nanosensor 1000 changes causing Wheatstone bridge 1200 to become unbalanced thereby creating a voltage between contacts 1212 and 1214. This sensed voltage change is detected to indicate a neuron firing event.

Although the present invention has been described with reference to preferred embodiments, workers skilled in the art will recognize that changes may be made in form and detail without departing from the spirit and scope of the invention.

What is claimed is:

1. An apparatus comprising:
   a substrate;
   a plurality of biological material stimulators positioned on the substrate, each biological material stimulator forming a fluctuating magnetic field capable of interacting with biological material wherein each biological material stimulator comprises a magnetic structure in which a magnetic domain wall moves to produce the fluctuating magnetic field.

2. The apparatus of claim 1 wherein each biological material stimulator comprises a neuron stimulator capable of inducing a current in a neuron.

3. The apparatus of claim 1 wherein each biological material stimulator is controlled using light.

4. The apparatus of claim 1 further comprises at least one magnetic sensor positioned on the substrate and capable of determining when a neuron fires based on a magnetic field induced by the neuron.

5. The apparatus of claim 1 wherein the substrate is flexible.

6. The apparatus of claim 1 further comprising a power source and a wireless communication system positioned on the substrate.

7. A method comprising:
introducing an array of biological material stimulators mounted on a substrate into a living body;
applying signals to the array of biological material stimulators to cause the biological material stimulators to generate a fluctuating magnetic field that interacts with biological material surrounding the biological material stimulators wherein each biological material stimulator comprises a magnetic material and wherein each signal applied to each respective biological material stimulator causes at least one magnetic domain wall in the magnetic material of the respective biological material stimulator to move.

8. The method of claim 7 wherein the substrate is flexible.

9. The method of claim 7 wherein each biological material stimulator comprises a half loop of the magnetic material that extends upward from the substrate.

10. The method of claim 9 wherein each half loop of magnetic material has a height and at least two of the half loops of magnetic material have different heights from each other.

11. The method of claim 7 wherein introducing the biological material stimulators further comprises introducing a magnetic sensor mounted on the substrate with the biological material stimulators.

12. The method of claim 11 wherein the magnetic sensor comprises a magnetic tunnel junction.

13. The method of claim 7 wherein introducing the array of biological material stimulators comprises sealing the array of biological material stimulators in the living body without a wired connection between the array of biological material stimulators and an environment external to the living body.

14. A neuron stimulator comprising:
a substrate having an outer surface;
a magnetic nanowire extending transverse to the outer surface such that a top of the nanowire is above the substrate, the magnetic nanowire having at least two magnetic domains with at least one moveable domain wall between the magnetic domains.

15. The neuron stimulator of claim 14 wherein the substrate is flexible.

16. The neuron stimulator of claim 14 wherein the magnetic nanowire is one of a plurality of magnetic nanowires extending transverse to the outer surface.

17. The neuron stimulator of claim 16 wherein at least two of the plurality of magnetic nanowires extend different heights above the outer surface relative to each other.

18. The neuron stimulator of claim 14 further comprising a wireless power circuit capable of receiving power wirelessly.

19. The neuron stimulator of claim 14 further comprising at least one magnetic sensor positioned on the substrate.

20. The neuron stimulator of claim 19 further comprising a wireless communication system positioned on the substrate such that a sensed value from the at least one magnetic sensor is communicated through the wireless communication system to an external device.

* * * * *